US011590148B2

(12) United States Patent
Bishop et al.

(10) Patent No.: US 11,590,148 B2
(45) Date of Patent: Feb. 28, 2023

(54) USE OF CALCIFEDIOL IN BARIATRIC SURGERY PATIENTS

(71) Applicant: OPKO IRELAND GLOBAL HOLDINGS, LTD., Grand Cayman (KY)

(72) Inventors: Charles W. Bishop, Miami Beach, FL (US); Phillip Frost, Miami Beach, FL (US)

(73) Assignee: EIRGEN PHARMA LTD., Waterford (IE)

(*) Notice: Subject to any disclaimer, the term of this patent is extended or adjusted under 35 U.S.C. 154(b) by 0 days.

(21) Appl. No.: 16/374,348

(22) Filed: Apr. 3, 2019

(65) Prior Publication Data

US 2019/0298744 A1 Oct. 3, 2019

Related U.S. Application Data

(60) Provisional application No. 62/652,038, filed on Apr. 3, 2018.

(51) Int. Cl.
| | | |
|---|---|---|
| *A61K 31/593* | (2006.01) | |
| *A61K 9/00* | (2006.01) | |
| *A61K 9/48* | (2006.01) | |
| *A61P 3/02* | (2006.01) | |
| *A61P 3/14* | (2006.01) | |
| *A61K 47/10* | (2017.01) | |
| *A61K 9/16* | (2006.01) | |

(52) U.S. Cl.
CPC .......... *A61K 31/593* (2013.01); *A61K 9/0053* (2013.01); *A61P 3/02* (2018.01); *A61P 3/14* (2018.01); *A61K 9/0019* (2013.01); *A61K 9/1635* (2013.01); *A61K 9/48* (2013.01); *A61K 9/4858* (2013.01); *A61K 9/4866* (2013.01); *A61K 47/10* (2013.01)

(58) Field of Classification Search
CPC ................ A61K 31/593; A61K 9/0019; A61K 9/0053; A61K 9/1635; A61K 9/48; A61K 9/4858; A61K 9/4866; A61K 47/10; A61P 3/14; A61P 3/02
See application file for complete search history.

(56) References Cited

U.S. PATENT DOCUMENTS

| | | |
|---|---|---|
| 8,329,677 B2 | 12/2012 | Bishop et al. |
| 8,361,488 B2 | 1/2013 | Bishop et al. |
| 8,962,239 B2 | 2/2015 | Petkovich et al. |
| 9,426,391 B2 | 8/2016 | Takada et al. |
| 9,861,644 B2 | 1/2018 | White et al. |
| 2010/0093678 A1* | 4/2010 | Della-Fera .......... A61K 31/593 514/167 |
| 2010/0120728 A1 | 5/2010 | Petkovich et al. |
| 2010/0144684 A1 | 6/2010 | Bishop |
| 2013/0137663 A1 | 5/2013 | Messner et al. |

FOREIGN PATENT DOCUMENTS

| | | | | |
|---|---|---|---|---|
| WO | WO-2014143941 A1 * | 9/2014 | .......... | A61K 31/592 |
| WO | WO-2016/205245 A1 | 12/2016 | | |
| WO | WO-2017/182237 A1 | 10/2017 | | |

OTHER PUBLICATIONS

Ilic et. al., Endocrine Oncology & Metabolism, 2015, Assoc. for Endocrine Oncology & Metabolism, pp. 25-36 (Year: 2015).*
Muschitz et. al., Journal of Bone & Mineral Res., 2016, American Soc. for Bone & Mineral Res., vol. 31(3), pp. 672-682 (Year: 2016).*
Muschitz et. al., Journal of Bone & Mineral Res., published online Sep. 9, 2015, American Soc for Bone & Mineral Res., vol. 31(3), pp. 672-682 (Year: 2015).*
DailyMed, "Rayaldee label", U.S. National Lib. Med., publ. Apr. 30, 2021, pp. 1-4 (Year: 2021).*
Lanzarini et al., High-Dose Vitamin D Supplementation is Necessary After Bariatric Surgery: A Prospective 2-Year Follow-up Study, Obes. Surg., 25(9):1633-8 (Sep. 2015).
International Application No. PCT/IB2019/000572, International Search Report and Written Opinion, dated Sep. 26, 2019.
Alexandrou et al., "Determinants of Secondary Hyperparathyroidism in Bariatric Patients after Roux-en-Y Gastric Bypass or Sleeve Gastrectomy: A Pilot Study," International Journal of Endocrinology (2015).
Aman et al., "Early Hospital Readmission after Bariatric Surgery," Surg Endosc, 30:2231-2238 (2016).
Baretta et al., "Secondary Hyperparathyroidism after Bariatric Surgery: Treatment is with Calcium Carbonate or Calcium Citrate?" ABCD Arq Bras Cir Dig, 28(Supl. 1)43-45 (2015).
Brancatella et al., "Calcifediol Rather Than Cholecalciferol for a Patient Submitted to Malabsortive Bariatric Surgery: A Case Report," Journal of the Endocrine Society, 1(8):1079-1084 (2017).
Chakhtoura et al., "Hypovitaminosis D in bariatric surgery: A systematic review of observational studies," Metabolism, 65(4):574-585 (2016).
Dumon et al., "Bariatric Surgery Outcomes," Surg Clin N Am, 91:1313-1338 (2011).
Elder et al., "Bariatric Surgery: A Review of Procedures and Outcomes," Gastroenterology, 132:2253-2271 (2007).
Fliser et al., Fibroblast growth factor 23 (FGF23) predicts progression of chronic kidney disease: the mild to moderate kidney disease (MMKD) study, J. Am. Soc. Nephrol., 18:2601-8 (2007).
Ibrahim et al., Serum fibroblast growth factor-23 levels in chronic haemodialysis patients, *Int. Urol. Nephrol.*, 41:163-9 (2009).
Lehmann et al., "Coating of Tablets and Small Particles with Acrylic Resins by Fluid Bed Technology," *Int. J. Pharm. Tech. & Prod. Mfr.*, 2:31-43 (1981).
Nieves-Khouw et al., "Bariatric Surgery: Beyond Informed Consent," Bariatric Nursing and Surgical Patient Care, 4(3):191-202 (2009).
O'Brien, "Bariatric Surgery: Mechanisms, Indications and Outcomes," Advances in Clinical Practice, 25:1358-1365 (2010).
Panazzolo et al., "Hypoparathyroidism after Roux-en-Y Gastric Bypass—A Challenge for Clinical Management: A Case Report," Journal of Medical Case Reports, 8:357-341 (2014).

(Continued)

*Primary Examiner* — Sarah Pihonak
(74) *Attorney, Agent, or Firm* — Marshall, Gerstein & Borun LLP

(57) ABSTRACT

Methods and compositions for treating bariatric surgery patients, and for treating or preventing complications associated with such patients, are disclosed.

31 Claims, No Drawings

(56) References Cited

OTHER PUBLICATIONS

Parrott et al., "American Society for Metabolic and Bariatric Surgery Integrated Health Nutritional Guidelines for the Surgical Weight Loss Patient 2016 Update: Micronutrients," Surgery and Obesity and Related Diseases (2017).

Segaran, "Symposium 7: Downsize me Provision of Nutritional Support to Those Experiencing Complications Following Bariatric Surgery," Proceedings of the Nutrition Society, 69:536-542 (2010).

Serrano et al., "Weight Loss Outcomes and Complications from Bariatric Surgery in the Super Super Obese," Surg Endosc, 30:2505-2511 (2016).

Sharman et al., "Motivations for Seeking Bariatric Surgery: The Importance of Health Professionals and Social Networks," Bariatric Surgical Practice and Patient Care, 11(3):104-109 (2016).

Tanner et al., "Complications of Bariatric Surgery: Implications for the Covering Physician," The American Surgeon, 75(2):103-112 (2009).

Tashko "Vitamin D Alternative," (2017). Retrieved from the Internet at: URL:http://gertitashkomd.com/blog/2017/8/30/vitamin-d-alternative.

Tebben et al., Elevated fibroblast growth factor 23 in women with malignant ovarian tumors, *Mayo Clin. Proc.*, 80:745-51 (2005).

Zouridaki et al., "Dermatological Complications after Bariatric Surgery: Report of Two Cases and Review of the Literature," Dermatology, 228:5-9 (2014).

\* cited by examiner

USE OF CALCIFEDIOL IN BARIATRIC SURGERY PATIENTS

CROSS-REFERENCE TO RELATED APPLICATIONS

The application claims the priority benefit under 35 U.S.C. § 119(e) of U.S. Provisional Patent Application No. 62/652,038, filed Apr. 3, 2018, the disclosure of which is incorporated herein by reference in its entirety.

BACKGROUND

Field of the Disclosure

The disclosure relates generally to treatment of bariatric surgery patients with 25-hydroxyvitamin $D_3$. The disclosure also relates to treating or preventing one or more complications of vitamin D insufficiency or deficiency associated with obesity and bariatric surgery, for example secondary hyperparathyroidism and osteomalacia.

Brief Description of Related Technology

Bariatric surgery has been shown to be an effective intervention for weight reduction in obese patients. However, morbid obesity and subsequent surgical intervention often lead to nutritional deficiencies, including vitamin D deficiency, as measured by serum total 25-hydroxyvitamin D. A recent review paper (Chakhtoura et al., Metabolism, 65(4) p. 574-85, April 2016) reported mean pre-surgery 25-hydroxyvitamin D levels below 30 ng/mL in 29 of 51 observational studies, and mean 25-hydroxyvitamin D levels ≤20 ng/mL in 17 of those studies. Mean 25-hydroxyvitamin D levels remained below 30 ng/mL following bariatric surgery, despite various vitamin D supplementation regimens, with few exceptions.

The vitamin D deficiencies in this population results from several factors, including some related to obesity itself, others relating to the type of surgical intervention, and others relating to the consequences of surgical intervention. As to the first factor, an inverse correlation has been observed between body mass index (BMI) and serum total 25-hydroxyvitamin D. Despite normal absorption, obese patients have been shown to have decreased bioavailability of vitamin D, as a result of it being stored in fat, and low serum total 25-hydroxyvitamin D also has been proposed to be the result of volumetric dilution. Obese patients have also been shown to have decreased expression of 1α-hydroxylase and 25-hydroxylase in cutaneous and visceral adipose tissues. Bariatric surgery procedure has also been shown to influence serum total 25-hydroxyvitamin D level. In malabsorptive procedures, fat malabsorption is a contributor to deficiency of fat-soluble vitamin D. Bypass of one or more primary vitamin D absorption sites in the small intestine also contributes to vitamin D deficiency, as does impaired digestion. Dietary intolerance, associated with both bypass and restrictive procedures, can also contribute to vitamin D deficiency.

Vitamin D deficiency in this population has been associated with secondary hyperparathyroidism, osteomalacia, and other skeletal complications including bone loss, e.g. as evidenced by reduced bone mineral density.

Secondary hyperparathyroidism is a disorder which develops primarily because of Vitamin D deficiency. It is characterized by abnormally elevated blood levels of PTH and, in the absence of early detection and treatment, it becomes associated with parathyroid gland hyperplasia and a constellation of metabolic bone diseases. It is a reported complication of vitamin D deficiency associated with bariatric surgery. Production of Vitamin D prohormones (e.g., 25-hydroxyvitamin $D_3$) declines when Vitamin D is in short supply. Low production of Vitamin D prohormones leads to low blood levels of 25-hydroxyvitamin D.

Chronically low blood levels of 1,25-dihydroxyvitamin D can develop because of a deficiency of Vitamin D prohormones, since adequate renal hormone production cannot proceed without the required precursors. Prohormone production declines markedly when cholecalciferol and ergocalciferol are in short supply, a condition often described by terms such as "Vitamin D insufficiency," "Vitamin D deficiency," or "hypovitaminosis D." Reduced serum levels of 1,25-dihydroxyvitamin D cause increased, and ultimately excessive, secretion of PTH by direct and indirect mechanisms. The resulting hyperparathyroidism leads to markedly increased bone turnover and its sequela of renal osteodystrophy, which may include a variety of other diseases, such as, osteitis fibrosa cystica, osteomalacia, osteoporosis, extraskeletal calcification and related disorders, e.g., bone pain, periarticular inflammation and Mockerberg's sclerosis. Reduced serum levels of 1,25-dihydroxyvitamin D also can cause muscle weakness and growth retardation with skeletal deformities (most often seen in pediatric patients).

SUMMARY

One aspect of the disclosure provides a method for treating a patient having undergone bariatric surgery by administering sustained release 25-hydroxyvitamin $D_3$.

Another aspect of the disclosure provides a method for treating secondary hyperparathyroidism a patient having undergone bariatric surgery by administering sustained release 25-hydroxyvitamin $D_3$.

Another aspect of the disclosure provides a method for treating intractable vitamin D insufficiency (VDI) in a patient having undergone bariatric surgery by administering sustained release 25-hydroxyvitamin $D_3$ Intractable VDI is defined as serum total 25-hydroxyvitamin D below 30 ng/mL despite at least 3 months of treatment with a minimum of 3,000 IU per day of either cholecalciferol or ergocalciferol.

Another aspect of the disclosure provides a method for treating or preventing one or more conditions in a patient having undergone bariatric surgery by administering sustained release 25-hydroxyvitamin $D_3$, the conditions being one or more of renal osteodystrophy, osteomalacia, osteitis fibrosa cystica, osteoporosis, extraskeletal calcification, bone pain, periarticular inflammation, Mockerberg's sclerosis, muscle weakness, growth retardation, and skeletal deformities.

Another aspect of the disclosure provides a method of increasing bone mineral density a patient having undergone bariatric surgery by administering sustained release 25-hydroxyvitamin $D_3$.

Another aspect of the disclosure is preventing the development of more severe vitamin D deficiency and related secondary hyperparathyroidism caused by bariatric surgery by administering sustained release 25-hydroxyvitamin $D_3$ in advance of surgery.

For the methods, articles, and kits described herein, optional features, including but not limited to components, compositional ranges thereof, substituents, conditions, and steps, are contemplated to be selected from the various aspects, embodiments, and examples provided herein.

Further aspects and advantages will be apparent to those of ordinary skill in the art from a review of the following detailed description. While the methods are susceptible of embodiments in various forms, the description hereafter includes specific embodiments with the understanding that the disclosure is illustrative, and is not intended to limit the invention to the specific embodiments described herein.

DETAILED DESCRIPTION

Described herein are materials and methods for treating bariatric surgery patients, including treating or preventing one or more conditions in bariatric surgery patients post-surgery.

The materials and methods are contemplated to include embodiments including any combination of one or more of the additional optional elements, features, and steps further described below, unless stated otherwise.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

As used herein, "Vitamin D insufficiency and deficiency" is generally defined as having serum total 25-hydroxyvitamin D level below 30 ng/mL. Intractable VDI is defined as serum total 25-hydroxyvitamin D below 30 ng/mL despite at least 3 months of treatment with a minimum of 3,000 IU per day of either cholecalciferol or ergocalciferol.

As used herein "hypercalcemia" refers to condition in a patient wherein the patient has corrected serum level of calcium above 10.2 mg/dL. Normal corrected serum level of calcium for a human is between about 8.6 to 10.2 mg/dL. As used herein, "hypocalcemia" refers to a condition in a patient wherein the patient has corrected serum level of calcium below 8.6 mg/dL.

As used herein the term "hyperphosphatemia" refers to a condition in a patient having serum phosphorous level above 4.6 mg/dL.

As used herein the term 25-hydroxyvitamin D refers generically to forms of 25-hydroxyvitamin D, including 25-hydroxyvitamin $D_2$, 25-hydroxyvitamin $D_3$ and 25-hydroxyvitamin $D_4$. In any method described herein, it is contemplated that use of 25-hydroxyvitamin D can include, consist of, or consist essentially of a combination of 25-hydroxyvitamin $D_2$ and 25-hydroxyvitamin $D_3$. In any method described herein, it is contemplated that use of 25-hydroxyvitamin D can include, consist of, or consist essentially of 25-hydroxyvitamin $D_3$.

As used herein, the term "serum total 25-hydroxyvitamin D" refers to the sum of 25-hydroxyvitamin $D_2$ and 25-hydroxyvitamin $D_3$ in serum.

As used herein the term 1,25-dihydroxyvitamin D refers generically to forms of 25-hydroxyvitamin D, including 1,25-dihydroxyvitamin $D_2$, and 1,25-dihydroxyvitamin $D_3$.

The term "serum total 1,25-dihydroxyvitamin D" refers to the sum of 1,25-dihydroxyvitamin $D_2$ and 1,25-dihydroxyvitamin $D_3$ in serum.

While bariatric surgeries are commonly performed on obese patients for weight reduction intervention, the patient treated according to a method described herein can also be one who has had, for example a malabsorptive-associated surgery for another reason, e.g. intestinal cancer. Bariatric surgeries generally fall into two types, and combinations thereof: malabsorptive and restrictive. In malabsorptive procedures, ingested food bypasses absorptive and/or secretory areas of the stomach, small intestine, or both the stomach and small intestine. In restrictive procedures, the stomach's capacity is greatly reduced. The type of bariatric surgery can include, for example, one or more of gastric bypass, gastroplasty, biliopancreatic diversion, anastomosis, Roux-en-Y gastric bypass, gastroenterostomy, pancreaticojejunostomy, gastrectomy, and jejunoileal bypass. Specific procedures can include, but are not limited to, gastric bypass, sleeve gastrectomy, adjustable gastric band, and biliopancreatic diversion with duodenal switch.

For example, in gastric banding, e.g. adjustable gastric banding, a silicone band or inflatable band is placed around the upper stomach, creating a small stomach pouch above the band, with the remainder of the stomach below the band, connected to the small upper pouch via an opening. The size of the opening between the upper stomach pouch and the remainder of the stomach can be adjusted, for example, by filling the band with sterile saline, or removing saline from the band.

In Roux-en-Y gastric bypass, a small stomach pouch is created by dividing the top of the stomach from the rest of the stomach. Then, the first portion of the small intestine is divided, and the bottom end of the divided small intestine is brought up and connected to the newly created small stomach pouch. The procedure is completed by connecting the top portion of the divided small intestine to the small intestine further down so that the stomach acids and digestive enzymes from the bypassed stomach and first portion of small intestine will eventually mix with the food. Thereby, ingested food passes through the small stomach pouch and into the connected portion of the small intestine, thereby bypassing the distal portion of the stomach and the first portion of the small intestine. In one type of embodiment, the bypassed portion of the small intestine includes the duodenum. In another type of embodiment, the bypassed portion of the small intestine includes the duodenum and a proximal portion of the jejunum.

In sleeve gastrectomy, the stomach is divided, e.g. vertically. The volume of the stomach can be reduced by at least 70%, or 75%, or 80%, or 85%, for example. The pyloric valve is preserved.

In biliopancreatic diversion, a portion of the stomach, e.g. the distal horizontal section, is removed. The remaining part of the stomach is connected to the lower portion of the small intestine, e.g. bypassing all the duodenum, and optionally all or a portion of the jejunum, and optionally a proximal portion of the ilium.

In a biliopancreatic diversion with duodenal switch, a portion of the stomach is removed, creating a small pouch. The small intestine is divided into two parts. The distal end of the small intestine, often at the ilium, is connected to the stomach pouch, so that the proximal portion of the small intestine is bypassed. The excluded portion of the small intestine is connected to the small bowel, to form a common channel which flows into the colon.

Jejunoileal bypass is a strictly malabsorptive procedure. The stomach remains intact. Typically, a portion (e.g. 35 cm) of proximal jejunum is anastomosed to a terminal portion of the ileum (e.g., 10 cm).

As described above, bariatric surgery often bypasses the preferential site (i.e., duodenum) for calcium and vitamin D absorption, placing patients at risk for altered calcium and vitamin D homeostasis.

Bariatric surgery can be effective for treating obesity, but it is not without significant side effects. Macro and micronutrient deficits are common in bariatric patients, one of which is VDI. The cause of VDI in bariatric patients is complex and is related to obesity, as well as lifestyle and physiological factors beyond diet and nutrient malabsorption. Left untreated, VDI can lead to SHPT, muscle weakness and eventually bone disease.

Different factors ubiquitous in bariatric patients, beyond vitamin D malabsorption resulting from the bypass of primary absorption sites as well as impaired digestion, contribute to VDI. An inverse relationship between body mass index (BMI) and serum 25-hydroxyvitamin D levels has been demonstrated in multiple studies. Obesity limits mobility and thus it has been hypothesized that bariatric patients receive less sun exposure which is essential for the synthesis of vitamin $D_3$. Additionally, vitamin D is sequestered in adipose tissues and diluted in larger body masses. Obesity is also associated with decreased hepatic synthesis of the vitamin D prohormone, calcifediol (25-hydroxyvitamin $D_3$), and increased expression of the vitamin D catabolic enzyme CYP24A1. In one class of embodiments, the patient will be one who has undergone a surgery that includes an element of bypass. In one aspect, the bypass will include a distal portion of the stomach. In another aspect, the bypass will include all or a portion of the duodenum. In another aspect, the bypass will include both a distal portion of the stomach and all or a portion of the duodenum. In another aspect, the bypass will include at least a proximal portion of the jejunum. In another aspect, the bypass will include both the jejunum and all or a portion of the duodenum. In another aspect, the bypass will include a distal portion of the stomach, the duodenum, and at least a proximal portion of the jejunum.

The treatments described herein are contemplated for use in bariatric surgery patients post-surgery. In another embodiment, the treatments described herein are contemplated for use in bariatric surgery patients both before and post-surgery. The therapy can be used in such patients pre-surgery if desired, e.g. as part of a pre-surgery routine. For example, the pre-surgery treatment can be initiated when the patient is considering bariatric surgery. The pre-surgery treatment can be initiated when the patient is deemed eligible for bariatric surgery. In another example, the pre-surgery treatment can be initiated at the same time as other vitamin or multivitamin supplements as part of a pre-surgery regimen. In another example, the pre-surgery treatment can be initiated at the same time as a pre-surgery diet plan is initiated. As another example, the pre-surgery treatment can be initiated within a fixed time period before surgery, e.g. 6-months before surgery, 30 days before surgery, 2 weeks before surgery, five days before surgery, or on the day of surgery. Optionally in any of the foregoing methods, the treatment (pre- or post-surgery) can be initiated in a patient having serum total 25-hydroxyvitamin D level of 30 ng/mL or less, or less than 30 ng/mL, or 20 ng/mL or less, or less than 20 ng/mL. Optionally in any of the foregoing methods, the treatment (pre- or post-surgery) can be initiated in a patient having secondary hyperparathyroidism. Optionally in any of the foregoing methods, the treatment (pre- or post-surgery) can be initiated in a patient having a plasma intact parathyroid hormone (iPTH) level above the upper limit of the laboratory reference range.

The bariatric surgery patients can be selected based on BMI and/or additional factors. For example, the patient can be one who has a BMI of greater than 40, or at least 45, or at least 50, or in a range of 50 to 100. In the alternative, the patient can have a BMI of greater than 35 coupled with one or more obesity-related diseases (e.g. heart disease, fatty liver, type 2 diabetes). In another embodiment, the patient can be one having a BMI of greater than 30 and undergoing a low-risk and/or low-invasiveness procedure, e.g. a gastric band procedure. In another embodiment, the patient can be one classified as more than 100 lbs (about 45 kg) overweight. In another embodiment, the patient can have a BMI of less than 30 and have vitamin D insufficiency. In another embodiment, the patient can have a BMI of less than 30 and have secondary hyperparathyroidism. In another embodiment, the patient can have a BMI of less than 30 and both vitamin D insufficiency and secondary hyperparathyroidism.

The patient to be treated by a method described herein can be one having decreased expression of 25-hydroxylase in cutaneous and/or visceral adipose tissues. The patient to be treated by a method described herein can be one having decreased expression of 1α-hydroxylase in cutaneous and/or visceral adipose tissues. The patient to be treated by a method described herein can be one having decreased expression of hepatic 25-hydroxylase.

The patient to be treated by a method described herein can be one suffering from one or more conditions or disorders including one or more of osteomalacia, renal osteodystrophy, osteitis fibrosa cystica, osteoporosis, extraskeletal calcification, bone pain, periarticular inflammation, Mockerberg's sclerosis, muscle weakness, growth retardation, and skeletal deformities (e.g., often seen in pediatric patients). For example, the patient treated can be one diagnosed as having one or more of the foregoing conditions or disorders.

In another aspect, the method can include treating or preventing one or more conditions or disorders including one or more of osteomalacia, renal osteodystrophy, osteitis fibrosa cystica, osteoporosis, extraskeletal calcification, bone pain, periarticular inflammation, Mockerberg's sclerosis, muscle weakness, growth retardation, and skeletal deformities.

In a method according to the present disclosure, the patient is administered 25-hydroxyvitamin D (calcifediol) in an amount of 30 to 150 mcg on the average per day. Individual doses can be in a range of 5 to 1,000 mcg, for example. Calcifediol is more polar than vitamin D (cholecalciferol or ergocalciferol) and is, therefore, more readily absorbed in the gastrointestinal tract. Further, unlike vitamin D, calcifediol does not require hepatic 25-hydroxylation, which may be reduced in obese patients.

The 25-hydroxyvitamin D can be dosed on any suitable schedule. For example, the dosing schedule can be daily, or every other day, or three times per week, or weekly.

The 25-hydroxyvitamin D can be dosed with food, or without food, or without regard to food. In one type of embodiment, the 25-hydroxyvitamin D is dosed without food, e.g. at bedtime, to reduce variances in 25-hydroxyvitamin D absorption due to food and/or food intolerance.

The 25-hydroxyvitamin D can be dosed without concomitant vitamin D therapy, e.g. in the absence of administration of cholecalciferol, in the absence of administration of ergocalciferol, in the absence of administration of calcifediol, in the absence of calcifediol analogs, in the absence of administration of 1α-hydroxylated vitamin D compounds. In the alternative, the 25-hydroxyvitamin D can be dosed with up to 3,000 IU per day or 90,000 IU per month of vitamin D supplementation (i.e., total amount of cholecalciferol and ergocalciferol administered for supplementation).

The treatment can include administering 25-hydroxyvitamin D without concomitant calcimimetic therapy, e.g. in the absence of cinacalcet.

The treatment can include limiting elemental calcium (from diet and supplements) to ≤1500 mg per day.

The treatment can include administering 25-hydroxyvitamin D without concomitant bone metabolism therapies, e.g. in the absence of bone metabolism therapies, e.g. bisphosphonates, denosumab, teriparatide, preotact, and calcitonin.

Cytochrome P450 inhibitors, such as ketoconazole, atazanavir, clarithromycin, indinavir, itraconazole, nefazodone, nelfinavir, ritonavir, saquinavir, telithromycin or voriconazole, may inhibit enzymes involved in vitamin D metabolism (CYP24A1 and CYP27B1), and may alter serum levels of 25-hydroxyvitamin D. Dose adjustment of 25-hydroxyvitamin D administration may be required if a patient initiates or discontinues therapy with a strong CYP3A4 inhibitor.

Cholestyramine has been reported to reduce intestinal absorption of fat-soluble vitamins and may impair the absorption of 25-hydroxyvitamin D. Dose adjustment of 25-hydroxyvitamin D administration may be required if a patient initiates or discontinues therapy with cholestyramine.

Phenobarbital and other anticonvulsants or other compounds that stimulate microsomal hydroxylation reduce the half-life of 25-hydroxyvitamin D. Dose adjustment of 25-hydroxyvitamin D administration may be required if a patient initiates or discontinues therapy with phenobarbital or other anticonvulsants.

The patient can be one having a plasma iPTH ≥85 pg/mL at the initiation of therapy.

The course of 25-hydroxyvitamin D therapy, and/or dosing adjustments, can be continued to achieve one or more therapeutic benefits. For example, the method can include 25-hydroxyvitamin D therapy to increase serum total 25-hydroxyvitamin D to a level of at least 30 ng/mL, or at least 50 ng/mL, or at least 90 ng/mL, or at least 100 ng/mL, or greater than 100 ng/mL, or in a range of 100 ng/mL to 200 ng/mL, or to maintain serum total 25-hydroxyvitamin D to a level of at least 30 ng/mL, or at least 50 ng/mL, or at least 90 ng/mL or at least 100 ng/mL, or greater than 100 ng/mL, or in a range of 100 ng/mL to 200 ng/mL. In another aspect, the method can include 25-hydroxyvitamin D therapy to increase serum total 25-hydroxyvitamin D by an at least 8 ng/mL, or greater than 8 ng/mL, or greater than 10 ng/mL, or greater than 15 ng/mL, or greater than 20 ng/mL, or greater than 30 ng/mL, for example in a range of 8 ng/mL to 200 ng/mL, or 15 ng/mL to 200 ng/mL. The method can include 25-hydroxyvitamin D therapy to increase serum total 25-hydroxyvitamin D to such levels and/or by such amounts at 6 months post operatively, for example. The method can include 25-hydroxyvitamin D therapy to increase serum total 25-hydroxyvitamin D to such levels and/or by such amounts at 6 months following the start of 25-hydroxyvitamin D therapy, for example.

The method can include 25-hydroxyvitamin D therapy to reduce serum parathyroid hormone level. The method can include 25-hydroxyvitamin D therapy to reduce serum parathyroid hormone level by at least 10%, or at least 20%, or at least 30% or more, compared to pre-treatment baseline. The method can include 25-hydroxyvitamin D therapy to reduce serum parathyroid hormone level to a target level, e.g. to a range of about 10 pg/mL to 65 pg/mL in adults and about 9 pg/mL to 52 pg/mL in pediatric patients. The method can include 25-hydroxyvitamin D therapy to maintain serum parathyroid hormone level below a threshold, e.g. an intact parathyroid hormone level in serum in a range of about 10 pg/mL to 65 pg/mL in adults and about 9 pg/mL to 52 pg/mL in pediatric patients. The method can include 25-hydroxyvitamin D therapy to increase bone mineral density, e.g. to T-score of at least −2.5, or greater than −2.5, or at least −2.0, or at least −1.5, or at least −1.0 or greater than −1.0. The method can include 25-hydroxyvitamin D therapy to decrease the blood level of a bone resorption marker, e.g. one or more of PTHrP, serum fibroblast growth factor 23 (FGF23), NTX, C-terminal cross-linked telopeptide of type I collagen (CTx), and tartrate-resistant acid phosphatase 5b (TRAP-5b, a.k.a. TRAC-5b). The method can include 25-hydroxyvitamin D therapy to decrease the blood level of a bone formation marker, e.g. bone-specific alkaline phosphatase (BAP) or procollagen type 1 N-terminal propeptide (P1NP). For example, the blood level of a bone resorption or formation marker can be reduced to within the reference range for the laboratory measurement technique. In another aspect, the blood level of a bone resorption or formation marker can be reduced by at least about 10%, or at least about 20%, or at least about 30%.

The level of FGF23 in a biological sample obtained from a patient can be determined by a variety of techniques known to one skilled in the art. For example, concentrations of intact FGF-23 (iFGF23) and median C-terminal FGF-23 (cFGF23) can be measured using ELISA kits available from IMMUTOPICS (San Clemente, Calif., USA). Measurements of the foregoing species are preferably made as serum concentrations, although concentrations can be measured in plasma, serum or other bodily fluids (e.g., saliva) or tissues. Normal iFGF23 levels are in the range of 0 to 90 pg/mL for healthy adult humans (Fliser et al. J. Am. Soc. Nephrol. 18:2601-2608 (2007), Ibrahim et al. Int. Urol. Nephrol. 41(1):163-169 (2009)). Normal cFGF23 levels are in the range of 0 to 85 reference units (RU)/mL for healthy adult humans (Tebbin et al. Mayo Clin. Proc. 80(6):745-751 (2005)).

In another aspect, the method can include administering 25-hydroxyvitamin D therapy as described herein and in the absence of 1,25-dihydroxyvitamin D therapy.

While the 25-hydroxyvitamin D can be administered in any form or by any method, in one aspect the 25-hydroxyvitamin D can be administered by a modified release method and/or formulation, e.g. including a sustained and/or delayed release aspect. In another aspect, the 25-hydroxyvitamin D can be administered solely or primarily by a sustained release (a.k.a. extended release, or prolonged release) method and/or formulation. For example, the sustained release can be effected via an oral dosage form, or the sustained release can be effected via a transdermal patch. In another aspect, sustained delivery can be provided via slow injection of the compound over time, e.g. a slow push intravenous delivery.

In one type of embodiment, the 25-hydroxyvitamin D is administered orally. For example, the 25-hydroxyvitamin D can be administered in an oral sustained release formulation. In the alternative, the 25-hydroxyvitamin D can be administered in an oral immediate release formulation in multiple doses over an extended time period throughout a day, in order to produce a pharmacokinetic profile of serum 25-hydroxyvitamin D that is similar to that achieved by an oral sustained release formulation.

For example, a controlled release composition intended for oral can be designed to contain concentrations of 25-hydroxyvitamin $D_2$ and/or 25-hydroxyvitamin $D_3$ of 1 to 1000 µg per unit dose and prepared in such a manner as to effect substantially constant release of the 25-hydroxyvitamin $D_2$ and/or 25-hydroxyvitamin $D_3$ over an extended period of time, e.g. at least 4 hours, or at least 8 hours, or at least 12 hours, or at least 24 hours.

The preparation of a sustained release form of 25-hydroxyvitamin D suitable for oral administration can be carried out according to many different techniques. For example, one or more 25-hydroxyvitamin D compounds can be dispersed within a matrix, i.e., a chosen mixture of rate controlling constituents and excipients in selected ratios within the matrix, and optionally encased with a coating material. In another alternative, one or more of various coating techniques can be utilized to control the rate of the release of the 25-hydroxyvitamin D from the pharmaceutical formulation. For example, a gradual dissolution of a coating over time can expose the dosage form contents, optionally in a matrix, to the fluid of the local environment. In one type of embodiment, after a coating becomes permeable, 25-hydroxyvitamin D diffuses through the coating, e.g. from the outer surface of the matrix contained within the coating. When the surface of such a matrix becomes exhausted or depleted of 25-hydroxyvitamin D, the underlying stores begin to be depleted by diffusion through the matrix to the external solution. In another type of embodiment, release of 25-hydroxyvitamin D through a permeable coating or framework is influenced gradual disintegration or erosion of a matrix contained therein, e.g., via solubility of one or more components of the matrix. In another type of embodiment, release of 25-hydroxyvitamin D is by gradual disintegration or erosion of a matrix, e.g., via solubility of one or more components of the matrix and/or by lack of physical integrity, without any coating or other framework surrounding the matrix. The dosage form can optionally further comprise another active agent, in the same region or a different region from the 25-hydroxyvitamin D. For example, the additional active agent can include calcium.

In one aspect, a formulation provides one or more 25-hydroxyvitamin D compounds within a matrix that releasably binds the ingredients for sustained release, e.g., when exposed to the contents of the gastric tract, e.g. stomach, small intestine, or colon.

In one embodiment of the invention, a controlled release oral formulation of 25-hydroxyvitamin D is prepared generally according to the following procedure. A sufficient quantity of 25-hydroxyvitamin D, e.g. calcifediol, is completely dissolved in a minimal volume of USP-grade absolute ethanol (or other suitable solvent) and mixed with appropriate amounts and types of pharmaceutical-grade excipients to form a matrix which is solid or semi-solid at both room temperature and at the normal temperature of the human body. The matrix gradually disintegrates in the intestine and/or colon.

In a suitable formulation, the matrix binds the 25-hydroxyvitamin D compound(s) and permits a slow, relatively steady, e.g. substantially constant, release of 25-hydroxyvitamin D over a period of four to eight hours or more, by simple diffusion and/or gradual disintegration, into the contents of small intestine and/or colon.

As discussed above, the means for providing the controlled release of 25-hydroxyvitamin D may be selected from any suitable controlled release delivery system, including any of the known controlled release delivery systems of an active ingredient over a course of about four or more hours, including the wax matrix system, and the EUDRAGIT RS/RL system (Rohm Pharma, GmbH, Weiterstadt, Germany).

The wax matrix system provides one type of a lipophilic matrix. The wax matrix system may utilize, for example, beeswax, white wax, cachalot wax or similar compositions. In one type of embodiment, the wax is a non-digestible wax, e.g. paraffin. The active ingredient(s) are dispersed in the wax binder which slowly disintegrates in intestinal fluids to gradually release the active ingredient(s). The wax binder that is impregnated with 25-hydroxyvitamin D can be loaded into softgel capsules. A softgel capsule may comprise one or more gel-forming agents, e.g., gelatin, starch, carrageenan, and/or other pharmaceutically acceptable polymers. In one embodiment, partially crosslinked soft gelatin capsules are used. As another option, vegetable-based capsules can be used. The wax matrix system disperses the active ingredient(s) in a wax binder which softens at body temperature and slowly disintegrates in intestinal fluids to gradually release the active ingredient(s). The system suitably can include a mixture of waxes, with the optional addition of oils, to achieve a melting point which is higher than body temperature, but lower than the melting temperature of the selected formulations used to create the shell of a soft or hard capsule, or vegetable capsule shell, or other formulation used to create a shell casing or other coating.

Specifically, in one suitable embodiment, the waxes selected for the matrix are melted and thoroughly mixed. The desired quantity of oils is subsequently added, followed by sufficient mixing for homogenization. The waxy mixture is then gradually cooled to a temperature just above its melting point. The desired amount of 25-hydroxyvitamin D, dissolved in ethanol, is uniformly distributed into the molten matrix, and the matrix is loaded into capsules, for example vegetable-based or gelatin-based capsules. The filled capsules optionally are treated for appropriate periods of time with a solution containing an aldehyde, such as acetaldehyde, to partially crosslink a polymer, e.g., gelatin, in the capsule shell, when used. The capsule shell becomes increasingly crosslinked, over a period of several weeks and, thereby, more resistant to dissolution in the contents of stomach and upper intestine. When properly constructed, this gelatin shell will gradually dissolve after oral administration and become sufficiently porous (without fully disintegrating) by the time it reaches the small intestine, to allow the 25-hydroxyvitamin D to diffuse slowly from the wax matrix into the contents of the small intestine and/or colon.

Examples of other lipid matrices suitable for use with the methods of the invention include one or more of glycerides, fatty acids and alcohols, and fatty acid esters.

A wax matrix can contain a stabilizing component to stabilize the release properties of the dosage form over its expected shelf life. The stabilizing component can be a cellulosic component, for example a cellulose ether, e.g. hydroxyl propyl methylcellulose.

In one embodiment, a formulation may comprise an oily vehicle for the 25-hydroxyvitamin D compound. Any pharmaceutically-acceptable oil can be used. Examples include animal (e.g., fish), vegetable (e.g., soybean), and mineral oils. The oil preferably will readily dissolve the 25-hydroxyvitamin D compound used. Oily vehicles can include non-digestible oils, such as mineral oils, particularly liquid paraffins, and squalene. The ratio between the wax matrix and the oily vehicle can be optimized in order to achieve the desired rate of release of the 25-hydroxyvitamin D compound. Thus, if a heavier oil component is used, relatively less of the wax matrix can be used, and if a lighter oil component is used, then relatively more wax matrix can be used.

Another suitable controlled-release oral drug delivery system is the EUDRAGIT RL/RS system in which the active 25-hydroxyvitamin D ingredient is formed into granules, e.g. having a dimension of 25/30 mesh. The granules are then uniformly coated with a thin polymeric lacquer, which is water-insoluble but slowly water-permeable. The coated granules can be mixed with optional additives including one or more of antioxidants, stabilizers, binders, lubricants, processing aids and the like. The mixture may be compacted into a tablet which, prior to use, is hard and dry and can be further coated, or it may be poured into a capsule. After the tablet or capsule is swallowed and comes into contact with the aqueous gastric and intestinal fluids, the thin lacquer begins to swell and slowly allows permeation by intestinal fluids. As the intestinal fluid slowly permeates the lacquer coating, the contained 25-hydroxyvitamin D is slowly released. By the time the tablet or capsule has passed through the small intestine, about four to eight hours or more later, the 25-hydroxyvitamin D will have been slowly, but completely, released. Accordingly, the ingested tablet will release a stream of 25-hydroxyvitamin D, as well as any other active ingredient.

The EUDRAGIT system is comprised of high permeability lacquers (RL) and low permeability lacquers (RS). RS is a water-insoluble film former based on neutral swellable methacrylic acids esters with a small proportion of trimethylammonioethyl methacrylate chlorides; the molar ratio of the quaternary ammonium groups to the neutral ester group is about 1:40. RL is also a water insoluble swellable film former based on neutral methacrylic acid esters with a small portion of trimethylammonioethyl methacrylate chloride, the molar ratio of quaternary ammonium groups to neutral ester groups is about 1:20. The permeability of the coating and thus the time course of drug release can be titrated by varying the proportion of RS to RL coating material. For further details of the Eudragit RL/RS system, reference is made to technical publications available from Rohm Tech, Inc. 195 Canal Street, Maiden, Mass., 02146 and K. Lehmann, D. Dreher "Coating of tablets and small particles with acrylic resins by fluid bed technology," *Int. J. Pharm. Tech. & Prod. Mfr.* 2(r), 31-43 (1981), incorporated herein by reference.

Other examples of insoluble polymers include polyvinyl esters, polyvinyl acetals, polyacrylic acid esters, butadiene styrene copolymers and the like.

The dosage forms may also contain adjuvants, such as preserving or stabilizing adjuvants. For example, a preferred formulation includes 25-hydroxyvitamin D (e.g., about 30 mcg, about 60 mcg, or about 90 mcg 25-hydroxyvitamin $D_3$), about 2 wt % anhydrous ethanol, about 10 wt % lauroyl polyoxylglycerides, about 20 wt % hard paraffin, about 23 wt % glycerol monostearate, about 35 wt % liquid paraffin or mineral oil, about 10 wt % hydroxypropyl methylcellulose, and optionally a small amount of antioxidant preservative (e.g., butylated hydroxytoluene). Formulations according to the invention may also contain other therapeutically valuable substances or may contain more than one of the compounds specified herein and in the claims in admixture.

As an alternative to oral 25-hydroxyvitamin D, intravenous administration of 25-hydroxyvitamin D is also contemplated. In one embodiment, the 25-hydroxyvitamin D is administered as a sterile intravenous bolus, optionally a bolus injection of a composition that results in a sustained release profile. In another embodiment, the 25-hydroxyvitamin D is administered via gradual injection/infusion, e.g., over a period of 1 to 5 hours, to effect controlled or substantially constant release of the 25-hydroxyvitamin D directly to DBP in the blood of the patient. For example, the composition may be injected or infused over a course of at least about 1 hour, at least about 2 hours, at least about 3 hours, at least about 4 hours, at least about 5 hours, or at least about 6 hours. In one embodiment, the composition intended for intravenous administration in accordance with the present invention is designed to contain a concentration of the 25-hydroxyvitamin D compound(s) of 1 to 100 mcg per unit dose. Sterile, isotonic formulations of 25-hydroxyvitamin D may be prepared by dissolving 25-hydroxyvitamin D in absolute ethanol, propylene glycol or another suitable solvent, and combining the resulting solution with one or more surfactants, salts and preservatives in appropriate volumes of water for injection. Such formulations can be administered slowly from syringes, for example, via heparin locks, or by addition to larger volumes of sterile solutions (e.g., saline solution) being steadily infused over time.

Suitable sustained release dosage forms of 25-hydroxyvitamin D have been described, including in the following U.S. patent and patent application publications, the disclosures of which are hereby incorporated by reference herein: 2010/0120728A1, 2010/0144684A1, 2013/0137663A1, U.S. Pat. Nos. 8,329,677, 8,361,488, 8,426,391, 8,962,239, and 9,861,644.

EXAMPLES

The following examples are provided for illustration and are not intended to limit the scope of the invention.

Example 1

Efficacy Study in Roux-en-Y Surgery Patients

The effectiveness of oral sustained-release 25-hydroxyvitamin $D_3$ in restoring serum total 25-hydroxyvitamin D to optimal levels (>30 ng/mL) and reducing parathyroid hormone level, is examined in a 6-month study of adult male and female patients who are candidates for Roux-en-Y Surgery for weight reduction. In a controlled study, patients are treated with sustained-release 25-hydroxyvitamin $D_3$ (softgel capsules containing 25-hydroxyvitamin $D_3$).

A total of 60 subjects participate in this study, all of whom have serum total 25-hydroxyvitamin D levels less than 30 ng/mL at the time of enrollment and serum intact parathyroid hormone levels greater than 70 pg/mL as evidence of SHPT. All subjects receive a multivitamin therapy including calcium (up to 1,000 mg daily) and cholecalciferol (3000 IU daily) following surgery, and abstain from receiving other Vitamin D therapy and significant sun exposure. Serum total 25-hydroxyvitamin D, serum intact parathyroid hormone, serum calcium, serum phosphorus, urinary calcium, urinary phosphorus, and urinary creatinine are measured from the day of surgery, and at monthly intervals following surgery.

After 2 months, the daily calcium dosage is maintained unchanged, and the cholecalciferol supplement is discontinued, while daily administration of sustained-release 25-hydroxyvitamin $D_3$ (softgel capsules containing 30 μg 25-hydroxyvitamin $D_3$) is initiated and continued for four months.

In measurements at time zero and months 1 and 2, the patient group's mean serum total 25-hydroxyvitamin D level is less than 30 ng/mL and the group's mean serum intact parathyroid hormone level is greater than 70 pg/mL. Following surgery, there is only a moderate increase in mean serum total 25-hydroxyvitamin D level, and no significant difference in serum intact parathyroid hormone level.

Following initiation of treatment with sustained-release 25-hydroxyvitamin D3, at month 3 there is a gradual but significant increase in the group's mean serum total 25-hydroxyvitamin D level and a progressive decrease in mean serum intact parathyroid hormone level. By the end of treatment at the month 6 measurement, the group's mean serum total 25-hydroxyvitamin D level is normalized to greater than 30 ng/mL, and the group's mean serum intact parathyroid hormone level is less than 65 pg/mL.

Example 2

Long-Term Efficacy Study in Roux-en-Y Surgery Patients

The effectiveness of oral sustained-release 25-hydroxyvitamin $D_3$ in restoring serum total 25-hydroxyvitamin D to optimal levels (>30 ng/mL) and increasing bone mineral density, is examined in a one year study of adult male and female patients having undergone bariatric surgery for weight reduction, wherein the surgery included bypass of at least the duodenum. In a randomized, double-blind controlled study, patients are treated with sustained-release 25-hydroxyvitamin $D_3$ or cholecalciferol.

A total of 200 subjects participate in this study. All subjects participating in this study are aged 18 years or older, have bone mineral density T-scores between −2.0 and −4.0 as assessed by dual energy x-ray absorptiometry (DEXA), and have serum total 25-hydroxyvitamin D levels less than 30 ng/mL at the time of enrollment. All subjects receive a multivitamin therapy including calcium (up to 1,000 mg daily) and either cholecalciferol (3000 IU daily) or multiple sustained-release 25-hydroxyvitamin $D_3$ (softgel capsules containing 30 μg 25-hydroxyvitamin $D_3$), and abstain from receiving other Vitamin D therapy and significant sun exposure at study start and continuing through study termination.

After 3 months, the daily 25-hydroxyvitamin $D_3$ softgel capsule dosage is maintained unchanged in patients whose serum total 25-hydroxyvitamin D is between 50 and 90 ng/mL, and increased by one capsule in patients whose serum total 25-hydroxyvitamin D is below 50 ng/mL. The dosage is immediately lowered by one capsule per day in patients whose serum total 25-hydroxyvitamin D rises above 100 ng/mL or whose serum calcium is confirmed above 10.3 mg/dL.

Serum total 25-hydroxyvitamin D, plasma iPTH, serum calcium, serum phosphorus, urinary calcium, urinary phosphorus, and urinary creatinine are measured from the day of surgery, and at monthly intervals. Bone mineral density at four sites (total hip, femoral neck, ⅓radius, and lumbar spine) is determined at quarterly intervals by DEXA.

After 6 to 9 months, all treated subjects exhibit serum total 25-hydroxyvitamin D levels that remain essentially stable with continuing dosing and rise to approximately 50 to 100 ng/mL with 25-hydroxyvitamin $D_3$ treatment or to approximately 5 to 25 ng/mL with Vitamin $D_3$ treatment. In patients treated with 25-hydroxyvitamin $D_3$, the incidence of hypocalcemia and severity of secondary hyperparathyroidism is markedly reduced once stable dosing has been achieved. However, in patients treated with cholecalciferol, hypocalcemia and secondary hyperparathyroidism occur more frequently. After 12 months of treatment, the patients treated with sustained-release 25-hydroxyvitamin $D_3$ are found to have higher and more consistent serum levels of 25-hydroxyvitamin $D_3$ and lower plasma iPTH levels than patients treated with cholecalciferol. Patients treated with sustained-release 25-hydroxyvitamin $D_3$ are also found to have significant increases in bone mineral density, compared to insignificant changes or reductions in bone mineral density for patients treated with cholecalciferol. Data from this study demonstrate that treatment with sustained-release 25-hydroxyvitamin $D_3$ is effective at normalizing serum total 25-hydroxyvitamin D, reducing plasma iPTH levels, and increasing bone mineral density without causing unacceptable side effects related to calcium, phosphorous or FGF23 metabolism.

Example 3

Long-Term Efficacy Study in Bariatric Surgery Patients

The effectiveness of oral extended-release 25-hydroxyvitamin $D_3$ (ERC) in raising serum total 25-hydroxyvitamin D to ≥30 ng/mL and reducing plasma iPTH by at least 30% from pre-treatement baseline is examined in a 52-week study of male and female patients aged at least 18 years, with intractable VDI, and having undergone bariatric surgery. In a randomized, double-blind controlled study, patients receive ERC or matching placebo.

Subjects are without any disease state or physical condition that might impair evaluation of safety or which would interfere with study participation, including having serum albumin ≤3.0 g/dL; and serum transaminase (alanine aminotransferase [ALT], glutamic-pyruvic transaminase [SGPT], aspartate aminotransferase [AST] or glutamic-oxaloacetic transaminase [SGOT])>2.5 times the upper limit of normal at screening.

During the initial screening visit, subjects exhibit plasma iPTH ≥70 pg/mL if receiving cinacalcet, calcitriol or other 1α-hydroxylated vitamin D analog (paricalcitol or doxercalciferol); or plasma iPTH ≥85 pg/mL if not receiving cinacalcet, calcitriol or other 1α-hydroxylated vitamin D analog (paricalcitol or doxercalciferol); and, serum total 25-hydroxyvitamin D <30 ng/mL.

When otherwise confirmed eligible at Visit 1, subjects forgo any further treatment with cinacalcet for the duration of the study and undergo an 8-week washout period.

When otherwise confirmed eligible at Visit 1, subjects forgo any further treatment with calcitriol or other 1α-hydroxylated vitamin D analogs for the duration of the study and undergo an 8-week washout period.

When otherwise confirmed eligible at Visit 1, if taking vitamin D supplementation at a rate of >3,000 IU per day or 90,000 IU (2,250 mcg) per month, subjects reduce the dose to ≤3,000 IU per day for the duration of the study and undergo an 8-week washout period.

Subjects exhibit, after the 8-week washout period if required due to prior use of cinacalcet, calcitriol or other 1α-hydroxylated vitamin D analogs, or vitamin D supplementation at a rate of >3,000 IU per day or 90,000 IU (2,250 mcg) per month: plasma iPTH ≥85 pg/mL pg/mL; corrected serum calcium <9.8 mg/dL; serum total 25-hydroxyvitamin D <30 ng/mL; and, serum phosphorus ≤5.5 mg/dL.

When otherwise confirmed eligible at Visit 1, if taking more than 1,500 mg per day of elemental calcium (from diet and supplements), subjects reduce calcium use (to ≤1,500 mg per day) for the duration of the study.

When otherwise confirmed eligible at Visit 1, if taking bone metabolism therapies that may interfere with study endpoints, subjects discontinue use of these agents for the duration of the study.

Subjects undergo a 6-week follow-up (FU) observation period after completing treatment. Thus, subjects will participate in the study for up to 70 weeks (2 weeks screening, 8 weeks washout, if required, 2 weeks baseline, 52 weeks of treatment with either ERC capsules or matching placebo, and 6 weeks of FU evaluation).

Blood samples are collected at weekly, biweekly or monthly intervals during the pre-treatment period, the 52-week treatment period, the 6-week post-treatment FU period, and at early termination (ET), if applicable. Key parameters analyzed in the collected samples include: plasma iPTH, serum calcium (corrected for serum albumin), serum phosphorus, serum total 25-hydroxyvitamin D, serum calcifediol, serum 1,25-dihydroxyvitamin $D_3$, and serum 24,25-dihydroxyvitamin $D_3$ ($24,25D_3$). Vital signs (VS), and AEs are monitored at each study visit. Other parameters monitored less frequently include brief physical examinations (PEs) and clinical laboratory tests (hematology and clinical chemistries). Electrocardiograms (ECGs; 12-lead) and bone mineral density assessments (by DEXA) are obtained at baseline and the end of treatment (EOT) only, or at ET. Additional parameters, including serum FGF23 and serum bone turnover markers are monitored at specified intervals.

Subjects initiate dosing with three capsules (two ERC capsules, 30 mcg strength, plus one matching placebo capsule, or three placebo capsules) per day at bedtime. After 12 weeks of treatment, subjects who are receiving ERC undergo upward dose titration from 60 mcg to 90 mcg per day (three ERC capsules, 30 mcg strength) provided that (a) the plasma iPTH has not decreased by at least 30% from pre-treatment baseline and remains >70 pg/mL, (b) corrected serum calcium is <9.8 mg/dL, and (c) serum phosphorus is ≤5.5 mg/dL.

Subjects reduce the dose at any time in increments of 30 mcg (one ERC capsule) per day in the event that plasma iPTH is confirmed to be <30 pg/mL, corrected serum calcium is confirmed to be >10.3 mg/dL, or serum phosphorus is confirmed to be >5.5 mg/dL, provided that the investigator has deemed the elevated serum phosphorus to be related to study drug administration. When a dose reduction is required for a subject receiving the minimum dosage of 30 mcg per day, the subject suspends dosing and resumes when iPTH is ≥30 pg/mL and corrected serum calcium is <9.8 mg/dL at the minimum dosage of 30 mcg per day. A subject who is receiving the minimum dosage of 30 mcg per day and who requires a second suspension of dosing forgoes further treatment with ERC capsules and immediately enters the FU period. Upward dose titration is not permitted at any time after a dose reduction.

Subjects assigned to ERC capsules suspend dosing if plasma iPTH is confirmed to be <15 pg/mL or corrected serum calcium is confirmed to be >11.0 mg/dL, and resume when plasma iPTH is ≥30 pg/mL and corrected serum calcium is <9.8 mg/dL at a dose that has been reduced by 30 mcg per day or at the minimum dosage of 30 mcg per day. Subjects receive three placebo capsules per day during any suspension of dosing.

Subjects do not take any vitamin D and/or bone metabolism therapy other than ERC and vitamin D supplementation at a rate ≤3,000 IU per day. Excluded therapies include 1α-hydroxylated vitamin D analogs (calcitriol, paricalcitol and doxercalciferol), cinacalcet, bisphosphonates, denosumab, teriparatide, preotact, calcitonin and other drugs that may affect bone metabolism. Glucocorticoids and hormone replacement therapy remain at the same dose throughout the study. Use of calcium supplements or calcium-based antacid therapies such as calcium carbonate or calcium acetate is allowed up to 1000 mg per day of elemental calcium. There are no study specific dietary restrictions. Subjects follow their dietary plan if one has been prescribed. Subjects maintain their usual pattern of sun exposures and activities.

After treatment, all treated subjects exhibit serum total 25-hydroxyvitamin D levels that remain essentially stable with continuing dosing and rise to approximately 50 to 100 ng/mL with 25-hydroxyvitamin $D_3$ treatment or to approximately 5 to 25 ng/mL with Vitamin $D_3$ treatment. In patients treated with 25-hydroxyvitamin $D_3$, the incidence of hypocalcemia and severity of secondary hyperparathyroidism is markedly reduced once stable dosing has been achieved. However, in patients treated with cholecalciferol, hypocalcemia and secondary hyperparathyroidism occur more frequently. After 12 months of treatment, the patients treated with sustained-release 25-hydroxyvitamin $D_3$ have higher and more consistent serum levels of 25-hydroxyvitamin $D_3$ and lower plasma iPTH levels than patients treated with cholecalciferol. Patients treated with sustained-release 25-hydroxyvitamin $D_3$ have significant increases in bone mineral density, compared to insignificant changes or reductions in bone mineral density for patients treated with cholecalciferol. Data from this study demonstrate that treatment with sustained-release 25-hydroxyvitamin $D_3$ is effective at normalizing serum total 25-hydroxyvitamin D, reducing elevated plasma iPTH and increasing bone mineral density without causing unacceptable side effects related to calcium, phosphorus, or FGF23 metabolism.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A method of treating a bariatric surgery patient having a BMI of greater than 30, comprising administering to the patient an effective amount of 25-hydroxyvitamin D wherein the 25-hydroxyvitamin D is administered in the form of a sustained release oral capsule comprising 25-hydroxyvitamin $D_3$ and a waxy carrier in a wax matrix.

2. The method of claim 1, comprising treating vitamin D insufficiency and/or vitamin D deficiency in the patient.

3. The method of claim 2, comprising treating intractable vitamin D insufficiency.

4. The method of claim 1, comprising treating or preventing a condition in the patient selected from one or more of secondary hyperparathyroidism, osteomalacia, renal osteodystrophy, osteitis fibrosa cystica, osteoporosis, extraskeletal calcification, bone pain, periarticular inflammation, Mockerberg's sclerosis, muscle weakness, growth retardation, and skeletal deformities.

5. The method of claim 1, wherein the bariatric surgery comprises a malabsorptive component.

6. The method of claim 1, wherein the bariatric surgery comprises a bypass component.

7. The method of claim 6, wherein at least the patient's duodenum is bypassed.

8. The method of claim 7, wherein at least the patient's duodenum and at least a portion of the patient's jejunum is bypassed.

9. The method of claim 8, wherein at least the patient's duodenum and jejunum are bypassed.

10. The method of claim 1, wherein the bariatric surgery patient has undergone Roux-en-Y surgery.

11. The method of claim 1, comprising administering the 25-hydroxyvitamin $D_3$ pre-surgery.

12. The method of claim 1, wherein the patient is classified as more than 100 lbs (45 kg) overweight.

13. The method of claim 1, comprising raising the patient's serum total 25-hydroxyvitamin D to greater than 30 ng/mL.

14. The method of claim 1, comprising lowering the patient's plasma intact parathyroid hormone level or lowering the patient's plasma intact parathyroid hormone level by at least 30%.

15. The method of claim 1, wherein the patient is an adult patient and comprising lowering the patient's plasma intact parathyroid hormone level to a range of 10 pg/mL to 65 pg/mL, or the patient is a pediatric patient and comprising lowering the patient's plasma intact parathyroid hormone level to a range of 9 pg/mL to 52 pg/mL.

16. The method of claim 1, comprising increasing the patient's bone mineral density, optionally to T-score of at least −2.5, or greater than −2.5, or at least −2.0, or at least −1.5, or at least −1.0 or greater than −1.0, as assessed by dual energy x-ray absorptiometry.

17. The method of claim 1, comprising reducing the blood level of a bone resorption marker in the patient.

18. The method of claim 17, wherein the bone resorption marker is one or more marker selected from PTHrP, FGF23, NTX, CTX, and TRAP-5b.

19. The method of claim 17, wherein the reduction is to within the normal reference range for the marker.

20. The method of claim 17, wherein the reduction is by at least about 10%, or at least about 20%, or at least about 30%.

21. The method of claim 1, comprising reducing the blood level of a bone formation marker in the patient.

22. The method of claim 21, wherein the bone formation marker is one or more marker selected from BAP and P1NP.

23. The method of claim 21, wherein the reduction is to within the normal reference range for the marker.

24. The method of claim 21, wherein the reduction is by at least about 10%, or at least about 20%, or at least about 30%.

25. The method of claim 1, wherein the oral dosage form comprises an amount of 25-hydroxyvitamin $D_3$ in a range of 1 μg to 1000 μg.

26. The method of claim 1, wherein the treatment simultaneously avoids causing hypocalcemia in the patient.

27. The method of claim 1, wherein the treatment simultaneously avoids causing hypercalcemia in the patient.

28. The method of claim 1, wherein the treatment simultaneously avoids increasing FGF23 in the patient.

29. The method of claim 1, wherein the patient has a plasma iPTH value of at least 85 pg/mL at the initiation of therapy.

30. A method of treating secondary hyperparathyroidism in a bariatric surgery patient having a BMI of greater than 30, comprising administering to the patient an effective amount of 25-hydroxyvitamin D wherein the 25-hydroxyvitamin D is administered in the form of a sustained release oral capsule comprising 25-hydroxyvitamin $D_3$ and a waxy carrier in a wax matrix, to lower the patient's plasma intact parathyroid hormone level.

31. A method of treating secondary hyperparathyroidism and vitamin D insufficiency or deficiency in a bariatric surgery patient having a BMI of greater than 30 and an iPTH value of at least 85 pg/mL, comprising administering to the patient an effective amount of 25-hydroxyvitamin D wherein the 25-hydroxyvitamin D is administered in the form of a sustained release oral capsule comprising 25-hydroxyvitamin $D_3$ and a waxy carrier in a wax matrix, to lower the patient's plasma intact parathyroid hormone level by at least 30%.

* * * * *